(12) United States Patent
Thiebaut et al.

(10) Patent No.: US 9,215,921 B2
(45) Date of Patent: Dec. 22, 2015

(54) PACKAGING AND APPLICATOR DEVICE INCLUDING AN APPLICATOR MEMBER

(75) Inventors: Laure Thiebaut, Paris (FR); Sylvain De Raemy, Cormeilles en Parisis (FR)

(73) Assignee: L'OREAL, Paris (FR)

( * ) Notice: Subject to any disclaimer, the term of this patent is extended or adjusted under 35 U.S.C. 154(b) by 564 days.

(21) Appl. No.: 13/520,585

(22) PCT Filed: Jan. 5, 2011

(86) PCT No.: PCT/IB2011/050040
§ 371 (c)(1),
(2), (4) Date: Feb. 12, 2013

(87) PCT Pub. No.: WO2011/083427
PCT Pub. Date: Jul. 14, 2011

(65) Prior Publication Data
US 2013/0189017 A1    Jul. 25, 2013

Related U.S. Application Data

(60) Provisional application No. 61/308,366, filed on Feb. 26, 2010, provisional application No. 61/308,350, filed on Feb. 26, 2010.

(30) Foreign Application Priority Data

Jan. 6, 2010 (FR) ..................................... 10 50060
Jan. 6, 2010 (FR) ..................................... 10 50061

(51) Int. Cl.
*B43K 1/06* (2006.01)
*A45D 40/26* (2006.01)
(Continued)

(52) U.S. Cl.
CPC ................ *A45D 40/26* (2013.01); *A45D 34/04* (2013.01); *A45D 2200/051* (2013.01); *A61N 1/0428* (2013.01); *A61N 1/303* (2013.01)

(58) Field of Classification Search
CPC .. A45D 34/04; A45D 40/26; A45D 2200/051
USPC ......................................... 401/262, 265, 266
See application file for complete search history.

(56) References Cited

U.S. PATENT DOCUMENTS 2,579,202 A    12/1951    Piccoli
3,750,255 A     8/1973    Stanley
(Continued)

FOREIGN PATENT DOCUMENTS

CN          1256674 Y      6/2000
CN       201006804 Y       1/2008
(Continued)

OTHER PUBLICATIONS

Chinese Office Action dated Jul. 10, 2014 for Chinese Application No. 201180005308.
(Continued)

*Primary Examiner* — Jennifer C Chiang
(74) *Attorney, Agent, or Firm* — Pearne & Gordon LLP

(57) ABSTRACT

A packaging and applicator device for applying at least one cosmetic, makeup, or care product composition, the device comprising: a container containing the composition; and an applicator member that is secured to the container and that defines an application surface, the applicator member being made, at least in part, out of an inorganic material, and having at least one channel passing therethrough so as to enable the composition to pass from the container to the application surface; the application surface having a surface area lying in the range 50 mm$^2$ to 200 mm$^2$, better in the range 70 mm$^2$ to 150 mm$^2$, better still in the range 80 mm$^2$ to 100 mm$^2$, and the applicator member having a weight that is greater than 4 g.

24 Claims, 4 Drawing Sheets

(51) Int. Cl.
  *A45D 34/04*   (2006.01)
  *A61N 1/04*    (2006.01)
  *A61N 1/30*    (2006.01)

(56)        References Cited

U.S. PATENT DOCUMENTS

| | | | |
|---|---|---|---|
| 3,987,790 | A | 10/1976 | Eckenhoff |
| 4,844,250 | A * | 7/1989 | Holoubek et al. ............ 222/107 |
| 6,338,414 | B1 | 1/2002 | Schellenbach |
| 7,281,876 | B2 * | 10/2007 | Kwon ............................ 401/265 |
| 7,883,287 | B2 * | 2/2011 | Thorpe ........................ 401/266 |
| 8,226,318 | B1 * | 7/2012 | Williams ...................... 401/266 |
| 8,517,622 | B2 * | 8/2013 | Apodaca et al. ............. 401/262 |
| 8,573,874 | B2 * | 11/2013 | Neuner ......................... 401/261 |
| 2008/0063464 | A1 * | 3/2008 | Prague ......................... 401/262 |
| 2008/0101850 | A1 * | 5/2008 | Wojcik et al. ................ 401/265 |
| 2008/0247809 | A1 * | 10/2008 | Bloc et al. .................... 401/266 |
| 2009/0103970 | A1 * | 4/2009 | Lee ............................... 401/262 |
| 2009/0297252 | A1 * | 12/2009 | Prague ......................... 401/265 |
| 2013/0108349 | A1 | 5/2013 | Thorpe |

FOREIGN PATENT DOCUMENTS

| | | |
|---|---|---|
| CN | 101301140 A | 11/2008 |
| EP | 0475426 A1 | 3/1992 |
| EP | 1797847 | 6/2007 |
| EP | 1797847 A1 | 6/2007 |
| FR | 2894460 | 6/2007 |
| FR | 2894460 A1 | 7/2007 |
| FR | 2915972 | 11/2008 |
| FR | 2915972 A1 | 11/2008 |

OTHER PUBLICATIONS

International Search Report for PCT/IB2011/050040 dated Jun. 28, 2011.

* cited by examiner

PACKAGING AND APPLICATOR DEVICE INCLUDING AN APPLICATOR MEMBER

The present invention relates to packaging and applicator devices for applying a cosmetic, makeup, or care-product composition, e.g. for application to the skin, and more particularly to devices comprising an applicator member comprising an inorganic material, so as to create a cold sensation on application.

In order to create a cold sensation, patent applications EP 1 797 847 and FR 2 894 460 propose using an applicator that is cooled beforehand by being put into a refrigerator or freezer, or by being exposed to an endothermic reaction or to a compressed or liquefied gas expanding.

U.S. Pat. No. 3,750,255 teaches using the thermal effusivity of an applicator ball to create a cold sensation on application. An example is given with a solid steel ball having a diameter of 32 millimeters (mm) and weighing 141 grams (g). The drawback of such a device is its weight, since the weight of the container containing the composition for application is additional to the weight of the ball. The cost of the device may also be relatively high as a result of the quantity of metal used.

Patent application FR 2 915 972 relates to a dispenser with a heat-storing endpiece that is made out of a metal such as Zamak®, and having a weight that lies in the range about 0.3 g to 0.6 g. Such a weight may turn out to be too light to make it possible to benefit from a sufficient cold sensation.

Patent application EP 0 475 426 relates to a viscous-liquid applicator that includes a movable applicator member that may be made out of various materials, preferably out of certain plastics materials. That member may fail to obtain a sufficient cold sensation.

There exists a need to improve still further packaging and applicator devices comprising an applicator member in order to benefit from a device that is capable of producing a cold sensation that is not too short-lasting, without needing to be placed beforehand in a refrigerator or a freezer, and that is of a weight that is acceptable and of a cost that is compatible with large-scale distribution.

Exemplary embodiments of the invention seek to satisfy this need, and they achieve this by means of a packaging and applicator device for applying at least one cosmetic, makeup, or care-product composition, the device comprising:

a container containing the composition; and
an applicator member that is secured to the container and that defines an application surface, the applicator member being made, at least in part, out of an inorganic material, and having at least one channel passing therethrough so as to enable the composition to pass from the container to the application surface;
the application surface having a surface area lying in the range 50 square millimeters ($mm^2$) to 200 $mm^2$, better in the range 70 $mm^2$ to 150 $mm^2$, better still in the range 80 $mm^2$ to 100 $mm^2$; and
the applicator member having a weight that is greater than 4 g.

The inorganic material may be selected from among: metals; ceramics; glasses; in particular metal-plated ceramics or glasses.

The applicator member may be made, at least in part, or even entirely out of a metal.

By means of the invention, it is possible to benefit from a device that is capable of producing a sufficient cold sensation that is linked to the thermal effusivity of the material of the applicator member. In the meaning of the invention, the cold sensation is sufficient when it has a duration that is greater than 10 seconds (s), or even greater than 15 s, e.g. a duration lying in the range at least 10 s to 20 s, better when it is maintained for the entire duration of the application.

The material for the applicator member may be selected so as to preserve a contact temperature that is less than the temperature of the skin, e.g. less than about 36° C. for at least 25 s, starting with an applicator member at 20° C. and with skin at 32° C., in an outside environment at 20° C.

The applicator of the invention makes it possible to obtain a cold sensation that is satisfactory to the user without unduly increasing the cost of the device. The cold may provide a decongestive and relaxing effect, advantageously being used while applying a cosmetic composition, so as to improve the application of the composition, in particular the comfort in application and the treatment or makeup effect of the composition.

The applicator member may be configured in such a manner that the temperature of the application surface does not rise by more than 5° C. to 10° C. for the duration of application, i.e. for a duration lying in the range 5 s to 30 s.

The applicator member of the invention further makes it possible to provide a sliding sensation that is better than that of an applicator that is made out of a thermoplastic material.

The applicator member is preferably stationary at least in translation relative to the container.

The channel may have a length l, measured along the longitudinal axis X of the device, that is greater than a greatest transverse dimension D of the channel, measured perpendicularly to the axis X, or even greater than 2D, better greater than 3D, so as to impart a sufficient cold effect.

The term "application surface" means the surface that comes into contact with the body during application, and that is for receiving the composition. By way of example, the application surface may be a front face of the applicator member when the device is observed along the longitudinal axis.

The term "inorganic" should be understood to mean other than a hydrocarbon or a silicone material, in particular other than a thermoplastic material. Advantageously, the inorganic material is non-particulate. The term "non-particulate" should be understood to mean other than a filler of a powder dispersed in a binder, such as a resin or a thermoplastic material.

In exemplary embodiments, the inorganic material is harder than the thermoplastic material of a closure cap.

The material of the applicator member may advantageously have a thermal conductivity that is greater than 1 watt per meter per kelvin ($Wm^{-1}K^{-1}$), better greater than 10 $Wm^{-1}K^{-1}$, better still greater than 20 $Wm^{-1}K^{-1}$.

The applicator member may be made entirely out of one or more inorganic materials. The inorganic material may be selected from among: metals; ceramics; glasses; in particular metal-plated ceramics or glasses. The applicator member may be made entirely out of a single inorganic material, e.g. a metal. The applicator member may be made, at least in part, or even entirely out of a metal.

The metal may be selected from among: steel; stainless steel, in particular E302, E304, E316, 201; aluminum; copper; silver; iron; alloys, in particular brass, bronze, Zamak®. The applicator member may be plated with another metal.

The material may be mainly in a non-oxidized form.

The applicator member may be completely inert from a chemical point of view, relative to the composition and relative to the skin.

The applicator member may be a single piece. The applicator member may be solid. The applicator member may be made entirely out of the inorganic material.

The applicator member may be machined. The surface of the applicator member may be a developable surface, i.e. the applicator member need not have a non-machinable recess.

The applicator member need not be covered by a varnish. It need not be galvanized. It need not be made by molding, in particular it need not be made by injection-molding. The applicator member may be made by machining a metal bar.

The material may define the visible surface of the applicator member, thereby obtaining maximum benefit from its thermal properties, e.g. by direct contact with the skin. The outside surface of the applicator member may be metal as a result of the applicator member being manufactured entirely out of metal, or as a result of the presence of a deposit of metal on its surface.

The outside surface of the applicator member may be smooth or rough. Among other possible surface states, the outside surface of the applicator member may be polished and reflective, for example. A smooth surface may be preferred for certain applicators, e.g. for applying a contour concealer composition for the eyes or a composition for the lips.

At least the application surface of the applicator member may be polished.

The application surface may have a surface roughness lying in the range 0.3 micrometers ($\mu m$) to 1.6 $\mu m$, better in the range 0.3 $\mu m$ to 0.8 $\mu m$.

The weight of the applicator member may be greater than or equal to 4.2 g, better greater than or equal to 4.5 g, better still greater than or equal to 5 g. In exemplary embodiments, the weight of the applicator member may lie in the range 6.9 g to 7.4 g, for example. The weight of the applicator member may be less than or equal to 15 g, better less than or equal to 12 g, better less than or equal to 10 g.

The weight of the applicator member may correspond to its weight of metal for an applicator member that is made entirely out of metal.

Empty of composition, the total weight of the device may be less than or equal to 15 g.

In order to make the applicator member, it is possible to use a material having thermal effusivity E that is greater than or equal to 1100 joules per square meter per kelvin per root second ($Jm^{-2}K^{-1}s^{-0.5}$) better greater than or equal to 6000 $Jm^{-2}K^{-1}s^{-0.5}$.

The thermal effusivity E is defined by $E=\sqrt{\lambda \rho c}$, where $\lambda$ is thermal conductivity, $\rho$ density, and c specific heat capacity. By way of example, E lies in the range about 7100 to 14000 for steel, is about 24000 for aluminum, and is 400 for the skin. Other values are given in the table below.

| Material | Effusivity ($Jm^{-2}K^{-1}s^{-0.5}$) |
|---|---|
| Gold | 28000 |
| Platinum | 14000 |
| Stainless steel | 7100 to 11000 |
| Aluminum | 23700 |
| Copper | 37000 |
| Iron | 15800 |
| Cast iron | 12000 to 16000 |
| Inconel | 6200 to 7600 |
| Glass (fused silica) | 1500 |
| Concrete | 1200 to 2500 |

The temperature of the applicator member may be determined by Fourier's law that, under steady conditions, expresses the quantity of heat dQ that passes in the x direction through a surface area S of thickness dx during time dt:

$$dQ = -\lambda S \frac{dT}{dx} dt$$

where:
dQ: infinitesimal energy in joules;
$\lambda$: thermal conductivity of the material in $Wm^{-1}K^{-1}$;
S: area in square meters ($m^2$);
dt: infinitesimal time in seconds (s); and $$\frac{dT}{dx}: \text{temperature gradient.}$$

The infinitesimal energy in joules that may be absorbed by the applicator member is given by:

$$dM = MC \frac{dT}{dx} dt$$

where:
M is the weight of the applicator member (in kilograms (kg)); and
C is the specific heat of the material (490 steel, 890 aluminum).

The surface of the applicator member may include a biocidal material, e.g. silver or copper. Such a metal may be deposited in the form of a thin layer.

The applicator member may be snap-fastened on the container. The applicator member may comprise an annular groove that is formed by machining, and that is snap-fastened on an annular bead or on an annular rim of a neck of the container.

In a variant, the applicator member may be adhesively-bonded and set into the container, or it may be fastened in some other way.

In other exemplary embodiments, and independently or in combination with the above, the invention also provides a packaging and applicator device for applying at least one cosmetic, makeup, or care-product composition, the device comprising:
a container containing the composition; and
an applicator member that is secured to the container and that defines an application surface, the applicator member being made, at least in part, out of an inorganic material, and having at least one channel passing therethrough so as to enable the composition to pass from the container to the application surface, the applicator member having a weight that is greater than 4 g.

In other exemplary embodiments, and independently or in combination with the above, the invention also provides a packaging and applicator device for applying a cosmetic, makeup, or care-product composition, the device comprising:
a container containing the composition; and
a composition applicator member that is secured to the container, and that has at least one channel passing therethrough so as to enable the composition to pass from the container to the outside;
the applicator member being machined out of a block of inorganic material, e.g. a metal, e.g. stainless steel or aluminum.

The device may comprise a closure cap for closing the container, the container and the closure cap co-operating in such a manner as to close the device in leaktight manner. The closure cap may be arranged so as to enable the device to stand vertically, head-down, on a horizontal plane surface.

The device may comprise a closure cap making it possible to protect the applicator member between uses and/or making it possible to close the device in leaktight manner, and preferably both simultaneously.

Leaktight closure of the device may be provided between the container and the closure cap, set back from the application surface.

The term "set back" means lower than the application surface when the device is stood on a support in its normal storage position, head-up, i.e. closure cap at the top.

The seal set back from the application surface is preferably obtained by a thermoplastic-material portion of the closure cap bearing against a thermoplastic-material portion of the container.

In exemplary embodiments, the inorganic material of the applicator member is harder than the thermoplastic material of the closure cap.

The closure cap for closing the container may include a closure member for closing a dispenser orifice of the channel that opens out to the application surface, the closure not being leaktight or being likely to lose its leaktightness following creep of the material of the closure member.

Exemplary embodiments of the invention also provide packaging and applicator devices for applying a cosmetic, makeup, or care-product composition, the device comprising in known manner: a container containing the composition; an applicator member that has at least one channel passing therethrough so as to enable the composition to pass from the container to a dispenser orifice; and a closure cap for closing the container.

Such devices are frequently made leaktight at the dispenser orifice, e.g. by means of a pin that projects from the top wall of the cap and that comes to bear in the dispenser orifice of the applicator member when the cap is in place on the container.

Patent application FR 2 915 972 relates to a dispenser with a heat-storing endpiece that is made out of a metal such as Zamak®.

The dispenser orifice may be made out of a thermoplastic-material insert in which the closure pin is engaged. Provision may be made for the pin and the insert to be made out of an elastomer material so as to achieve leaktight closure.

The presence of the insert makes it possible to obtain satisfactory sealing, but complicates the manufacture of the device, and also decreases the weight of metal used to provide the cold effect.

Other known cold-effect devices comprise a metal ball turning in a housing. When the closure cap is screw-fastened on the container, the closure cap presses the ball into the bottom of its housing. However, this closure method is usable only for a ball.

There exists a need to improve still further cold-effect devices, and in particular to provide leaktight closure throughout their working life, even after a device has been opened or closed many times, while also being simple in construction.

Exemplary embodiments of the invention seek to satisfy this need and they achieve this by means of a packaging and applicator device comprising:
    a container containing the composition; and
    an applicator member that is secured to the container and that defines an application surface, the applicator member being made, at least in part, out of an inorganic material, and having at least one channel passing therethrough so as to enable the composition to pass from the container to a dispenser orifice that opens out to the application surface; and
    a closure cap for closing the container, the cap comprising a closure member for closing the dispenser orifice, closure not being leaktight or being likely to lose its leaktightness following creep of the material of the closure member;

leaktight closure of the device being provided between the container and the closure cap, set back from the application surface.

The invention enables the dispenser orifice to be closed in non-leaktight manner, either because the closure starts off leaktight when the closure cap is fastened at the factory, but then degrades as a result of creep of the thermoplastic material in contact with the harder application surface, or because the closure does not start off leaktight, e.g. because the closure member cannot be closed in leaktight manner as a result of its structure and/or its positioning.

The term "set back" means below the application surface when the device is stood on a support in its normal storage position, head-up, i.e. closure cap at the top.

The seal set back from the application surface is preferably obtained by a thermoplastic-material portion of the closure cap bearing against a thermoplastic-material portion of the container.

For example, the container may comprise a body and a neck that are interconnected via a shoulder against which the closure cap may come to bear, with sealing being provided by the closure cap bearing against the shoulder of the container.

The shoulder may extend in a plane that is perpendicular to the axis of the neck, in particular a horizontal plane. In this configuration, the closure cap may include a bottom edge of corresponding shape, e.g. extending in a plane that is perpendicular to the axis of the cap, in particular a horizontal plane, for co-operating with the shoulder of the container so as to provide leaktight closure. The bottom end edge of the cap may be defined by the end of a fastener skirt for fastening the cap on the container, e.g. a fastener skirt comprising a screw thread that enables co-operation with the container by screw-fastening.

In variant exemplary embodiments, the shoulder of the container may slope, in particular it may be conical. In this configuration, the closure cap may comprise a beveled bottom end edge of corresponding shape, e.g. situated at the end of a fastener skirt for fastening on the container, e.g. a fastener skirt comprising a screw thread that enables screw-fastening on the container.

In other variant exemplary embodiments, the container may comprise a neck having a top end edge against which the closure cap may come to bear, with sealing being provided by the closure cap bearing against the top end edge of the neck of the container.

The top edge of the neck may extend in a plane that is perpendicular to the axis of the neck, in particular a horizontal plane. In this configuration, the closure cap may comprise a corresponding intermediate shoulder that extends perpendicularly to the axis of the cap, in particular a horizontal plane, for co-operating with the top end edge of the neck of the container so as to provide leaktight closure. The intermediate shoulder may be situated in the closure cap above a fastener skirt for fastening on the container, e.g. a fastener skirt comprising a screw thread enabling screw-fastening on the container.

In a variant, the top edge of the neck may be beveled. In this configuration, the closure cap may also comprise a corresponding beveled portion, e.g. situated above a fastener skirt for fastening on the container, e.g. a fastener skirt comprising a screw thread that enables co-operation with the container by screw-fastening.

At least one of the closure cap and the container may comprise an annular bead for closing the device in leaktight manner, by being compressed axially while the container is being closed. The bead may be narrower than the end edge or the shoulder on which it rests, and also narrower than the shoulder or the end edge against which it comes to bear. By way of example, the bead may be situated on the neck of the container or on the shoulder of the container, or even on the closure cap, e.g. on the bottom edge of the closure cap or on an intermediate shoulder formed inside the closure cap. The bead is advantageously made out of the same thermoplastic material as the part that carries it.

The closure cap may comprise a sealing lip for co-operating with a neck of the container, when the closure cap is in place on the container, so as to close the device in leaktight manner. The sealing lip may be situated above a fastener skirt for fastening on the container, e.g. a fastener skirt comprising a screw thread enabling screw-fastening on the container.

The closure member of the closure cap may comprise a closure pin for closing the dispenser orifice. Closure need not be leaktight, in particular after first use of the device or after a plurality of uses of the device.

The closure pin may be engaged, at least in part, in the above-mentioned channel.

In variant exemplary embodiments, the closure member of the closure cap may comprise a block of an elastically-compressible cellular material that is situated in the top of the closure cap, for closing the dispenser orifice when the cap is in place on the container. Closure of the dispenser orifice by the cellular material need not be leaktight.

The closure cap and the container may co-operate by snap-fastening. In a variant, the closure cap and the container may co-operate by screw-fastening or by a bayonet-type fastening.

The closure cap may be arranged so as to enable the device to stand vertically, head-down, on a horizontal plane surface, without any composition leaking.

The protocol used for measuring sealing is as follows: put the parts half-filled with water head-down in a vacuum bell (with the water in contact with the sealing zones to be tested) and create relative suction of −400 millibars (mbar) for 10 s. The absence of any water leaking in these conditions corresponds to closure that is leaktight.

By way of example, the composition is a makeup and/or care-product composition, in particular a dark-circle or contour concealer composition for the eyes, or a composition for the lips, e.g. a lipstick, a lipgloss, or a care-product composition for the lips.

The composition may contain a volatile hydrocarbon solvent, or, on the contrary, it may have no such solvent.

The composition may comprise at least 30% by weight of water, or even at least 50%.

The invention can be better understood on reading the following detailed description of non-limiting embodiments thereof, and on examining the accompanying drawings, in which.

Figure 1:
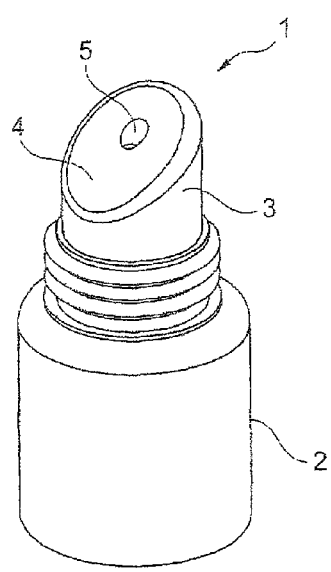
FIG. 1 is a diagrammatic and fragmentary elevation view of an example of a packaging and applicator device made in accordance with the invention.

FIGS. 1 to 4 show a packaging and applicator device 1 for applying a cosmetic, makeup, or care-product composition contained in a container 2 and for applying by means of an applicator member 3 that is secured to the container. The device extends along a longitudinal axis X.

The container 2 may be configured to encourage or to force the composition to flow towards the applicator member. For example, it may comprise a flexible tube for squeezing, a piston, a pump, or some other dispenser means. The composition may also flow by gravity and/or by capillarity.

The container may comprise a neck 15 on which the applicator member is fastened. In a variant, the container does not have a neck.

The neck 15 may be molded integrally with all or part of the container, e.g. by injection-molding or by injection blow molding. Alternatively, the neck 15 may be molded and fitted on the body of the container, and fastened thereto by snap-fastening, smoothing, heat-sealing, or adhesive. Alternatively, the neck may be molded onto the body of the container. Where appropriate, the container may have a separate bottom fitted thereto.

The container may form a flexible tube, or it may present a rigid body, e.g. a piston reservoir or a stick, or it may be made in some other way.

The applicator member 3 defines an application surface 4 of shape that is generally substantially plane in the embodiment described, but that could have some other shape, and that is supplied with composition via a channel 5 that is formed in the applicator member 3 so as to enable the composition to pass from the container to the application surface 4. The channel 5 opens out to the application surface via an orifice 6. The top end of the channel 5 defining the orifice 6 may be flared, as shown, e.g. being milled during machining of the applicator member 3.

The channel 5 may be of constant cross-section, or it may include two or more segments of different sections, e.g. a segment of smaller cross-section and a segment of larger cross-section, the segment of larger cross-section constituting a pilot hole for guiding the piercing of the segment of smaller cross-section.

The channel may have a length l, measured along the axis X, that is greater than 10 mm. The channel may have a greatest transverse dimension D, measured perpendicularly to the axis X, e.g. a diameter, lying in the range 1 mm to 3 mm.

The channel may have a length l that is greater than its greatest transverse dimension D, or even greater than 2D, better greater than 3D.

By way of example, the application surface 4 has a surface area of about 90 $mm^2$, e.g. lying in the range 80 $mm^2$ to 100 $mm^2$. Naturally, it would not be beyond the ambit of the present invention for the surface area of the application surface to be greater or smaller, e.g. lying in the range 70 $mm^2$ to 150 $mm^2$, or even in the range 50 $mm^2$ to 200 $mm^2$.

In the embodiment described, the application surface is bevel shaped, sloping by an angle lying in the range 30° to 70° relative to the longitudinal axis X of the device.

A greatest transverse dimension T of the applicator member, e.g. a diameter, may lie in the range 7 mm to 20 mm.

The greatest transverse dimension D of the orifice may be less than T/2, so as to impart a sufficient cold effect.

A height H of the applicator member, measured along the longitudinal axis X of the device, may lie in the range 7 mm to 20 mm.

The applicator member 3 is made out of an inorganic material, e.g. stainless steel. The choice of such a material makes it possible to guarantee a cold effect on application.

Figure 2:
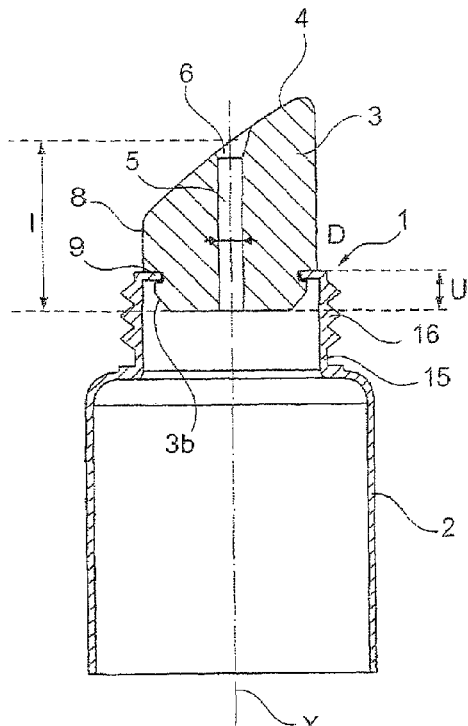
FIG. 2 is a diagrammatic and fragmentary section view on II-II in FIG. 1.
Figure 3:
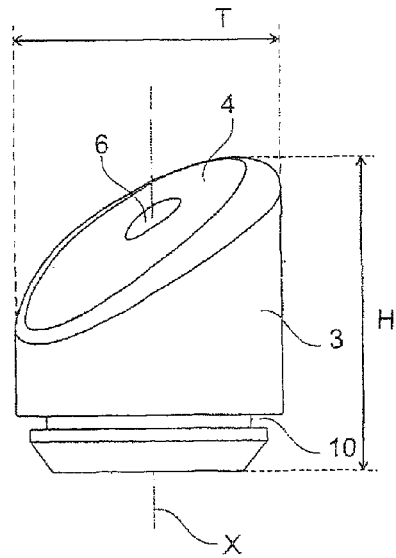
FIG. 3 is a diagrammatic and fragmentary elevation view of the FIG. 1 applicator member.
Figure 4:
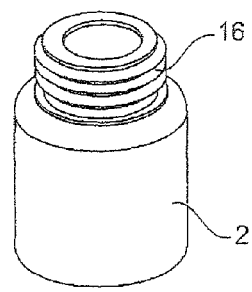
FIG. 4 is a diagrammatic and fragmentary elevation view of the FIG. 1 container.

This effect is guaranteed further by the fact that, in the embodiment described, the applicator member is made as a solid mass of the inorganic material, as can be seen in FIG. 2, being formed by an endpiece that is machined from a bar so that its outside surface 8 is developable.

The outside surface of the applicator member that is likely to come into contact with the body, e.g. that extends beyond the container, may have a surface area lying in the range 200 mm$^2$ to 700 mm$^2$.

Furthermore, the weight of the applicator member 3 is sufficient to ensure that the cold effect lasts long enough, i.e. throughout application, or at the very least for most of application, i.e. for a duration that is greater than 10 s, or even greater than 20 s.

By way of example, the weight of the applicator member lies in the range 5 g to 9 g, e.g. being about 6.4 g, but it would not be beyond the ambit of the present invention for it to be different and preferably greater than at least 4 g.

Furthermore, in the embodiment shown in FIGS. 1 to 4, the applicator member 3 is snap-fastened on the container 2, the container including for this purpose a collar 9, and the applicator member a corresponding annular groove 10, for example. The groove 10 may be machined, for example. The collar 9 is engaged in the groove 10. The collar may define the top end edge 30 of the neck 15 of the container.

The bottom end of the applicator member 3 may be beveled at 3b, so as to make it easier to insert into the neck.

Naturally, it would not be beyond the ambit of the present invention for the applicator member to be fastened to the container in some other way.

Figure 5:
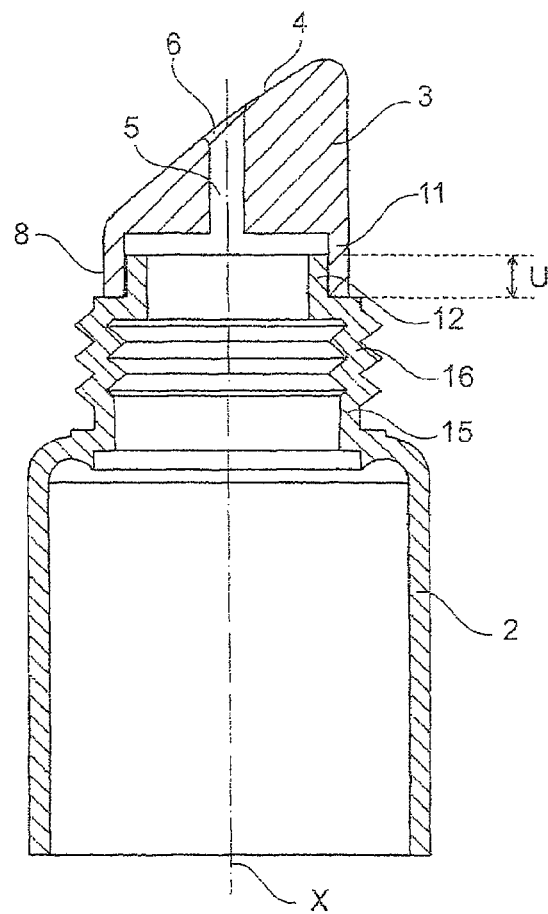
FIGS. 5 to 7 are views similar to FIGS. 2 to 4 of a variant embodiment of the invention.
Figure 6:
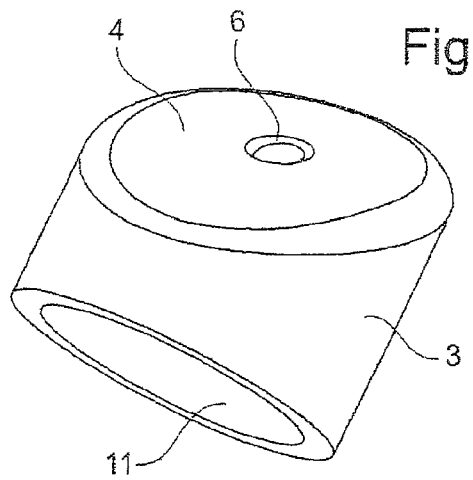
Figure 7:
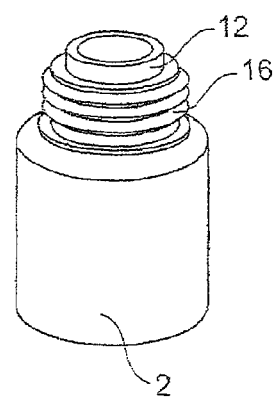

By way of example, FIGS. 5 to 7 show an embodiment in which the applicator member is adhesively-bonded on the container 2. To this end, the applicator member includes a fastener skirt 11 that comes to surround the top portion 12 of the neck 15 of the container 2.

By way of example, the fastener skirt may be engaged on or in the neck of the container over a distance U that is greater than 2 mm.

In the embodiments described above, the application surface 4 slopes relative to a longitudinal axis X of the device, which may make application easier. Furthermore, the application surface may be slightly convex and beveled at its periphery, as shown. Other shapes are possible.

The neck 15 may include a thread 16 for co-operating with a closure cap 20 of the device that is not shown in FIGS. 1 to 7. It is described in greater detail below.

Figure 8:
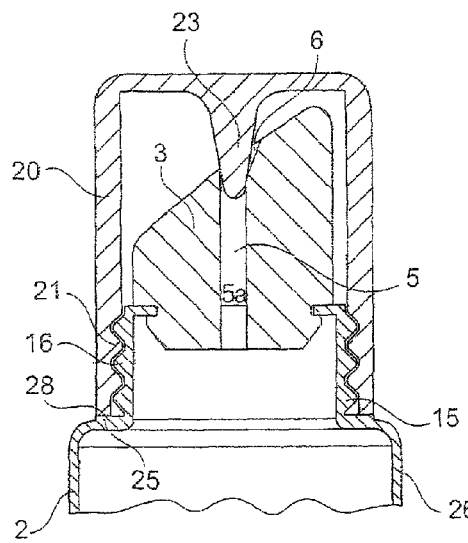
FIG. 8 is a diagrammatic and fragmentary section view similar to FIG. 2 showing a variant embodiment of the invention.

FIG. 8 shows the closure cap of the container of the embodiment in FIGS. 1 to 4. The closure cap 20 includes an internal thread 21 for co-operating with the thread 16 of the neck 15 of the container 2.

Furthermore, the cap 20 includes a closure member that, in the embodiment described, comprises a closure pin 23 that is connected to the top wall of the cap 20 in its central portion, and that is for plugging the orifice 6 of the channel 5 of the applicator member 3, as shown. The pin 23 does not come to be engaged along the entire length of the channel 5. It may penetrate into the channel 5 over a length s that is greater than 2 mm. It may be engaged in a circularly-cylindrical portion 5a of the channel 5 over a distance w that is greater than or equal to 1 mm. The pin 23 may be made by being molded integrally with the remainder of the cap 20. By way of example, it may be solid, being of shape that tapers. The applicator member may be in direct contact with the closure member.

However, in particular when the applicator member 3 is made out of an inorganic material that may be relatively hard, in particular compared to the material of the pin 23 that may be made out of a thermoplastic material, for example, driving the pin 23 into the orifice 6 does not enable the device to be closed lastingly in leaktight manner at the orifice 6. The pin 23 may be deformed on first use, or after a few uses, by its plastics material creeping.

The thermoplastic material of the pin 23 may for example be selected from the following non-limiting list: polyolefines; polyethylene (PE); polypropylene (PP); polyoxymethylene (POM); and acrylonitrile butadiene styrene (ABS).

Annular clearance may exist between the applicator member 3 and an inside surface 20a of the closure cap. The closure cap 20 may be configured to provide leaktight closure between the container and the closure cap, below the application surface.

To this end, the container may comprise a shoulder 25 that connects the neck 15 to the body 26 of the container 2, and the closure cap 20 may come to bear against the shoulder 25 via its bottom end edge 28, when the closure cap 20 is in place on the container 2.

Sealing may be provided by the closure cap 20 bearing against the shoulder 25 of the container when the closure cap 2 is fully screwed on the neck 15 of the container.

In the embodiment in FIG. 8, the shoulder 25 extends in a horizontal plane, and the same applies for the edge 28 of the closure cap.

Naturally, it would not be beyond the ambit of the present invention for the shoulder 25 to extend other than in a plane that is perpendicular to the longitudinal axis of the device.

Figure 9:
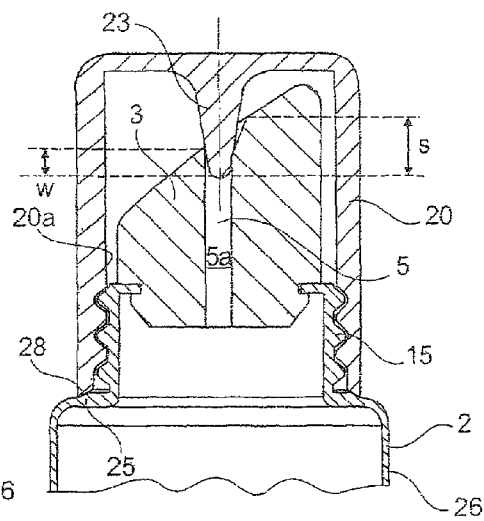
FIGS. 9 to 15 are views similar to FIG. 8, showing variant embodiments of the invention.

By way of example, FIG. 9 shows a variant embodiment in which the shoulder 25 slopes, including a conical portion that diverges on going away from the closure cap 20. In this configuration, the closure cap also includes a beveled edge 28 of corresponding shape.

In the two embodiments described above, sealing is provided at a shoulder of the container interconnecting the neck and the body of the container, but it would not be beyond the ambit of the present invention if this were otherwise.

Figure 10:
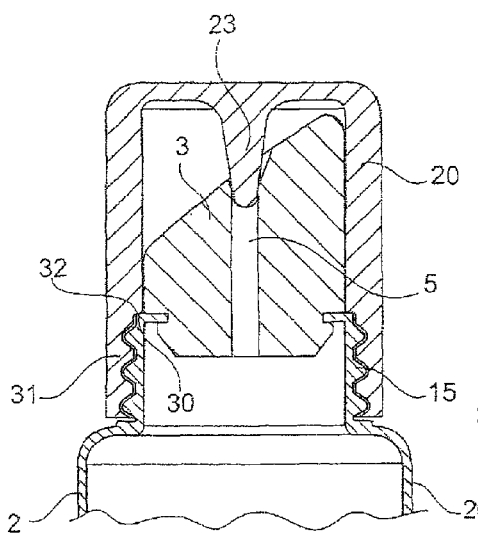
Figure 11:
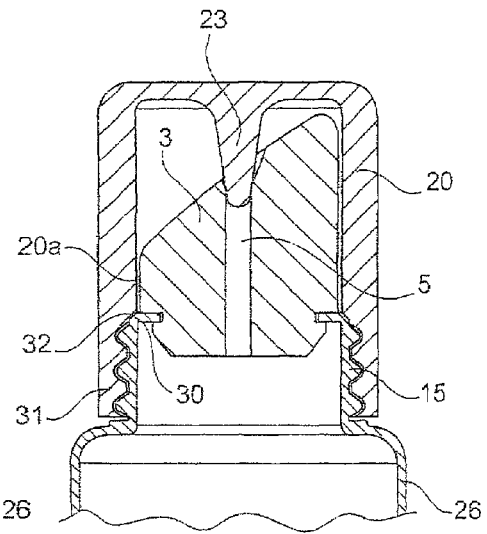

By way of example, FIGS. 10 and 11 show two variant embodiments in which sealing is obtained at an end edge 30 of the neck 15 of the container 2.

In the embodiment shown in FIG. 10, the end edge 30 extends in a horizontal plane that is perpendicular to the longitudinal axis X, the closure cap including a corresponding shoulder 32 that also extends in a horizontal plane. When the closure cap is fully screwed on, the shoulder 32 bears against the end edge 30 so as to close the container in leaktight manner.

The shoulder 32 is situated in the closure cap above a fastener skirt 31 that includes a thread 21 enabling screw-fastening on the container 2.

In the variant shown in FIG. 11, the end edge 30 of the neck of the container is conical, and the closure cap also includes a corresponding conical sealing portion that is situated above the fastener skirt 31.

Figures 12, 13:
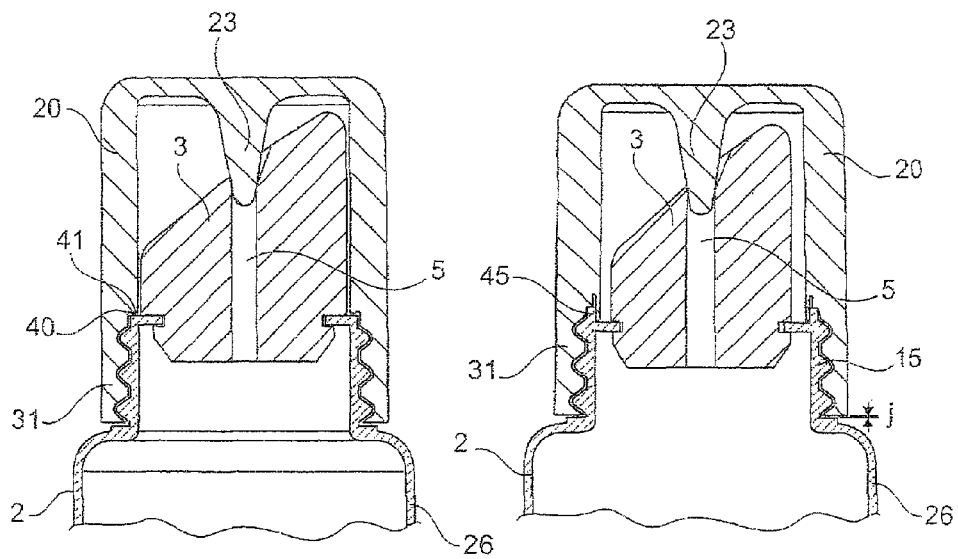

In another variant embodiment shown in FIG. 12, leaktight closure is provided by means of an annular bead 40 that is present on one of the closure cap and the container.

The annular bead 40 may be formed on a shoulder 41 that is disposed above the fastener skirt 31 of the cap, the bead coming to bear against the end edge 30.

In a variant, a bead is present on the neck of the container, or on the shoulder 25 of the container, or on the bottom end edge 28 of the closure cap, for example.

Still in a variant, the closure cap 20 comprises an annular sealing lip 45 for bearing against the inside surface of the neck 15, when the closure cap is in place on the container, so as to close the device in leaktight manner.

By way of example, the sealing lip 45 is situated above the fastener skirt 31, as shown in FIG. 13. In this figure, the device is shown with the closure cap fully screwed on the container. Clearance j may exist between the bottom edge of the cap and the shoulder at the base of the neck of the container. The portion in relief for snap-fastening the applicator member 3 on the container 2 may be situated above the bottom edge of the closure cap.

In all of the embodiments described above, the closure cap 20 and the container 2 co-operate by screw-fastening, but it would not be beyond the ambit of the present invention if this were otherwise.

Figures 14, 15:
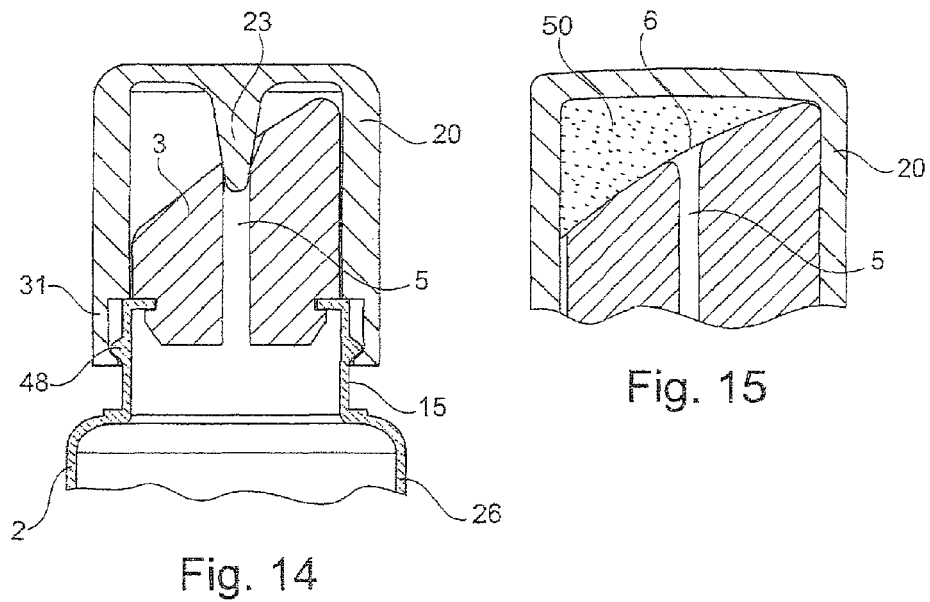

By way of example, FIG. 14 shows a variant embodiment in which the closure cap 20 and the container 2 co-operate by snap-fastening. To this end, on its neck 15, the container includes an annular bead 48, enabling the cap 20 to be snap-fastened by means of its fastener skirt 31 co-operating with the bead 48.

In all of the embodiments described above, the closure member of the closure cap comprises a pin 23, enabling the dispenser orifice 6 to be closed, with said closure not necessarily being leaktight, as described above.

Naturally, it would not be beyond the ambit of the present invention for the device to not have such a pin 23, the dispenser orifice 6 not being closed, or being closed by some other means.

By way of example, FIG. 15 shows a variant embodiment in which a block 50 of an elastically-deformable cellular material is disposed in the top of the cap 20, so as to enable the dispenser orifice 6 to be closed when the closure cap 20 is in place on the container.

In this embodiment, since the applicator member 3 has a truncated shape, the block 50 also has a truncated shape. The dispenser orifice 6 is closed by the applicator member 3 bearing against the surface of the block 50. Closure need not be leaktight.

Naturally, the invention is not limited to the embodiments shown.

By way of example, other materials may be used to make the applicator member, e.g. other metals such as aluminum, copper, silver, alloys, possibly a metal plated with a second metal.

The applicator member may be magnetic or non-magnetic. The device need not have a magnet.

When made out of metal, the applicator member may be used as a radiofrequency (RF) electrode, or as an electrode in an iontophoresis or electrophoresis method. The device may include a light source for performing an additional phototherapy treatment.

The expression "comprising a" should be understood as being synonymous with "comprising at least one".

The invention claimed is:

1. A packaging and applicator device for applying at least one cosmetic, makeup, or care-product composition, the device comprising:
   a container containing the composition;
   an applicator member that is secured to the container and that defines an application surface, the applicator member being made, at least in part, out of an inorganic material, and having at least one channel passing therethrough so as to enable the composition to pass from the container to the application surface, said channel being defined by said inorganic material, a top end of said channel forming a flared orifice;
   the application surface having a surface area lying in the range 50 mm$^2$ to 200 mm$^2$, and the applicator member having a weight that is greater than 4 g; and
   a closure cap for closing the container, the cap comprising a closure pin engaged at least in part in said channel.

2. A device according to claim 1, the applicator member being machined.

3. A device according to claim 1, wherein at least the application surface of the applicator member is polished.

4. A device according to claim 1, wherein the application surface has a surface roughness lying in the range 0.3 μm to 1.6 μm.

5. A device according to claim 1, wherein a length of the channel, measured along the longitudinal axis of the device, is greater than a greatest transverse dimension of the channel, measured perpendicularly to the axis, or even greater than 2D.

6. A device according to claim 1, the container and the closure cap co-operating in such a manner as to close the device in leaktight manner.

7. A device according to claim 1, wherein the applicator member is made entirely out of stainless steel or aluminum.

8. A device according to claim 1, wherein the applicator member is snap-fastened on the container, or is adhesively-bonded on the container.

9. A device according to claim 1 wherein said applicator member includes a wall that forms said channel and contacts the composition, said wall being comprised of said inorganic material.

10. A device according to claim 9 wherein said inorganic material is a metal.

11. A device according to claim 10 wherein said metal is stainless steel or aluminum.

12. A packaging and applicator device for applying a cosmetic, makeup, or care-product composition, the device comprising:
   a container containing the composition;
   a composition applicator member that is secured to the container, and that has a channel passing therethrough so as to enable the composition to pass from the container to the outside; said channel being defined by an inorganic material, a top end of said channel defining a flared orifice;
   the applicator member consisting essentially of said inorganic material; and
   a closure cap for closing the container, said cap comprising a closure pin engaged at least in part in said channel.

13. A device according to claim 12, wherein the applicator member is made entirely out of stainless steel or aluminum.

14. A packaging and applicator device for applying a cosmetic, makeup, or care-product composition, the device comprising:
   a container containing the composition;
   an applicator member that is secured to the container and that defines an application surface, the applicator member being made, at least in part, out of an inorganic material, and having at least one channel passing therethrough so as to enable the composition to pass from the container to a flared dispenser orifice formed by a top end of said channel that opens out to the application surface, said channel being defined by said inorganic material;
   and a closure cap for closing the container, the cap comprising a closure member for closing the dispenser orifice, the closure not being leaktight or being likely to lose its leaktightness following creep of the material of the closure member; a leaktight closure of the device being provided between the container and the closure cap, set back from the application surface, wherein the closure member comprises a closure pin engaged at least in part in said channel.

15. A device according to claim 14, the container comprising a body and a neck that are interconnected via a shoulder against which the closure cap may come to bear, with sealing being provided by the closure cap bearing against the shoulder of the container.

16. A device according to claim 15, the shoulder extending in a plane that is perpendicular to the axis of the neck, in particular a horizontal plane.

17. A device according to claim 15, the shoulder sloping, in particular being conical.

18. A device according to claim 17, the top edge of the neck being beveled.

19. A device according to claim 14, the container comprising a neck having a top end edge against which the closure cap may come to bear, with sealing being provided by the closure cap bearing against the top end edge of the neck of the container.

20. A device according to claim 19, the top edge of the neck extending in a plane that is perpendicular to the axis of the neck.

21. A device according to claim 14, at least one of the closure cap and the container comprising an annular bead for closing the device in leaktight manner, by being compressed axially while the container is being closed.

22. A device according to claim 14, the closure cap comprising a sealing lip for co-operating with a neck of the container, when the closure cap is in place on the container, so as to close the device in leaktight manner.

23. A device according to claim 14, the closure member of the closure cap comprising a block of an elastically-compressible cellular material that is situated in the top of the closure cap, for closing the dispenser orifice when the cap is in place on the container.

24. A device according to claim 14, the closure cap and the container co-operating by snap-fastening or by screw-fastening.

* * * * *